US00PP09759P

United States Patent [19]

Sapia

[11] Patent Number: Plant 9,759

[45] Date of Patent: Dec. 24, 1996

[54] CARNATION PLANT NAMED 'PACO'

[75] Inventor: Flavio Sapia, San Remo, Italy

[73] Assignee: Messick Company, Saratoga, Calif.

[21] Appl. No.: 517,110

[22] Filed: Aug. 21, 1995

[51] Int. Cl.[6] ..... A01H 5/00

[52] U.S. Cl. ..... Plt./70.7

[58] Field of Search ..... Plt./70.7

*Primary Examiner*—James R. Feyrer

*Attorney, Agent, or Firm*—Proprietary Rights International

[57] ABSTRACT

A distinct cultivar of Carnation plant named Paco, characterized by its red purple petal color; compact growth habit; freely branching habit; vigorous growth rate; proportional plant size; and floriferousness.

1 Drawing Sheet

The present invention relates to a new and distinct cultivar of Carnation plant, botanically known as *Dianthus caryophyllus,* and hereinafter referred to by the cultivar name Paco.

The new cultivar is a product of a planned breeding program conducted by the inventor in San Remo, Italy. The objective of the breeding program was to create new potted Carnation cultivars having different or more vivid flower colors.

The new cultivar originated from a cross made by the inventor of the proprietary selection of the breeder designated as V-79, as the male or pollen parent, with the propietary selection of the breeder designated as BB-1, as the female or seed parent.

The cultivar Paco was discovered and selected by the inventor as a flowering plant within the progeny of the stated cross in a controlled environment in San Remo, Italy. Asexual reproduction of the new cultivar by terminal cuttings taken at San Remo, Italy, has shonw that the unique features of this new Carnation are stabilized and reproduced true to type in successive generations.

The cultivar, Paco has not been observed under all possible environmental conditions. The phenotype may vary somewhat with variations in environment such as temperature, daylength and light intensity, without, however, any variance in genotype. The following observations, measurements and comparisons describe plants grown in Palisade, Colo. under commercial practice in a polyethylene-covered greenhouse.

The following traits have been repeated observed and are determined to be the unique characteristics of Paco. These characteristics in combination distinguish Paco as a new and distinct cultivar:

1. Red purple petal color.
2. Compact growth habit.
3. Freely branching habit.
4. Vigorous growth rate.
5. Proportional flowers to foliage ratio.
6. Floriferousness.

Compared to its parent, propietary selection V-79, the new Carnation is more compact, has larger flowers, and flower color is red purple compared to the lilac pink flower color of selection V-79. Compared to its parent, proprietary selection BB-1, the new Carnation is more freely branching and bushier, flowers two weeks earlier, and flower color is red purple compared to the pink flower color of selection BB-1.

Paco is most similar to the patented Carnation cultivar CFPC Cupid (U.S. Plant Pat. No. 8,419). However, the new Carnation differs from the cultivar CFPC Cupid in the following characteristics:

1. The petal color of plants of the new Carnation is darker red purple than the petal color of plants of the cultivar CFPC Cupid.

2. Flowers of plants of the new Carnation have fewer petals per flower, and petals are smaller than petals of plants of the cultivar CFPC Cupid.

3. Flowers of plants of the new Carnation are smaller in diameter than flowers of plants of the cultivar CFPC Cupid.

The accompanying colored photograph illustrates the overall appearance of the new cultivar, showing the colors as true as it is reasonably possible to obtain in colored reproductions of this type. The flower color appears more red than the actual flower color due to light reflectance. The photograph comprises a top perspective view of a flowering stem, flower, petals, flower bud and reproductive organs from a typical potted plant of Paco grown in a polyethylene-covered greenhouse in Palisade, Colo.

In the following description, color references are made to The Royal Horticultural Society Colour Chart except where general terms of ordinary dictionary significance are used. Measurements and numerical values represent averages for at least three typical plants grown in 10-cm containers with day temperatures of 24C., night temperatures of 18C., and a light level of 4,500 foot-candles.

Botanical classification: *Dianthus caryophyllus* cultivar Paco.

Parentage:

*Male.*—V-79, a propietary selection of the breeder.

*Female.*—BB-1, a propietary selection of the breeder.

Propagation:

*Type cutting.*—Terminal cuttings.

*Time to initiate roots.*—20 days at 21° C. soil temperature.

*Rooting habit.*—Numerous, fibrous, and well-branched.

Plant description:

*Form.*—Compact flowering potted plant.

*Habit of growth.*—Freely branching, bushy. Branching is increased by pinching.

*Plant height at flowering.*—Very compact, 12 cm.

*Vigor.*—Rapid growth rate.

*Foliage description.*—Leaves simple, opposite, generally symmetrical, abundant. Size: Length: 5 to 6 cm. Width: 1 cm. Shape: Narrow, lanceolate with acute leaf tip. Texture: Leathery, glabrous. Margin: Entire. Color: Young foliage top side: 143B. Young foliage under side: 143C. Mature foliage top side: 147A. Mature foliage under side: 147A. Stem color: 147A. Venation: Prominent mid-vein.

Flower description:

*Flower type and habit.*—Fully double flowers that are flat with an open center. Freely and continuously flowering.

*Inflorescences borne.*—Clusters of 3 to 5 flowers on strong peduncles borne above foilage, arising from terminal shoot and leaf axils. Flowers persistent and slightly fragrant.

*Flower longevity.*—14 to 16 days on the plant.

*Flower diameter.*—4 cm.

*Flower depth.*—3 cm.

*Flower buds.*—Shape: Cylindrical. Size: Length: 1.6 to 1.8 cm. Width (diameter): 8 mm. Opening rate: 4 to 5 days.

*Petals.*—Quantity: 22 to 24. Shape: Rounded fan-shaped. Tip: Finely serrated. Size: Length: 1.5 cm. Width: 1.7 cm. Color: Velvety appearance. Upper side, immature: 74A. Upper side, mature: 74A. Under side, mature: 60B. Fade: Petal color does not fade or discolor.

Calyx.—Shape: Cylindrical. Splitting: Not observed. Sepal quantity: 5. Sepal shape: Ovate. Sepal tip: Acute. Sepal size: Length: 1 cm. Width: 6 mm. Sepal color: Outside: 143B. Inside: 143C.

*Peduncle.*—Character: Stiff and upright. Color: 147A.

*Reproductive organs.*—Stamens: Arranged evenly around ovary. Stamen number: 18, petaloid. Filament: Petaloid. Anthers: None. Pollen: None. Pistils: Style length: 1 mm. Stigma color: Pink. Ovaries. 3.

Disease resistance: No known Carnation diseases observed to date.

Seed production: Not self-fertile. Fruit is spherical in shape and yellowish brown at maturity.

It is claimed:

1. A new and distinct cultivar of Carnation plant named Paco, as illustrated and described.

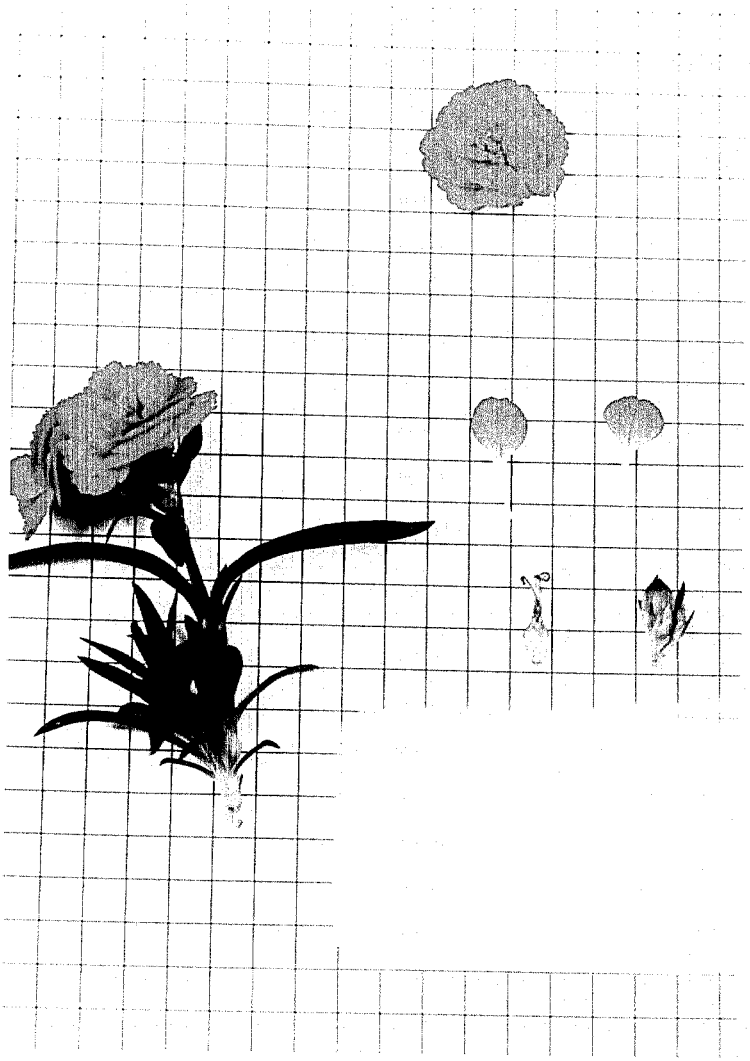

* * * * *